US00PP37779P3

(12) United States Plant Patent
Elstgeest

(10) Patent No.: US PP37,779 P3
(45) Date of Patent: Oct. 13, 2026

(54) ***MONSTERA* PLANT NAMED 'ELSTMN0424'**

(50) Latin Name: ***Monstera adansonii* Schott.**
Varietal Denomination: ELSTMN0424

(71) Applicant: ELSTGEEST YOUNG PLANTS HOLDING B.V., Rijsenhout (NL)

(72) Inventor: Debbie Elstgeest, Rijsenhout (NL)

(73) Assignee: Elstgeest Young Plants Holding BV, Rijsenhout (NL)

( * ) Notice: Subject to any disclaimer, the term of this patent is extended or adjusted under 35 U.S.C. 154(b) by 52 days.

(21) Appl. No.: 19/348,189

(22) Filed: Oct. 2, 2025

(65) Prior Publication Data

US 2026/0231843 P1 Aug. 6, 2026

(30) Foreign Application Priority Data

Feb. 4, 2025 (QZ) ..... PBR 2025/0241

(51) Int. Cl.
*A01H 6/10* (2018.01)
*A01H 5/12* (2018.01)

(52) U.S. Cl.
USPC ..... Plt./373

(58) Field of Classification Search
USPC ..... Plt./373
CPC ..... A01H 6/10; A01H 5/12
See application file for complete search history.

*Primary Examiner* — Keith O. Robinson
(74) *Attorney, Agent, or Firm* — James R. Holm; Plant Novelty Rights, LLC

(57) ABSTRACT

A new and distinct *Monstera* plant named 'ELSTMN0424' particularly distinguished by leaves with numerous small-sized fenestrations creating a denser and more perforated leaf appearance, a medium green leaf coloration with no variegation, and a compact and trailing growth habit with pendulous branches.

2 Drawing Sheets

Figure 1:
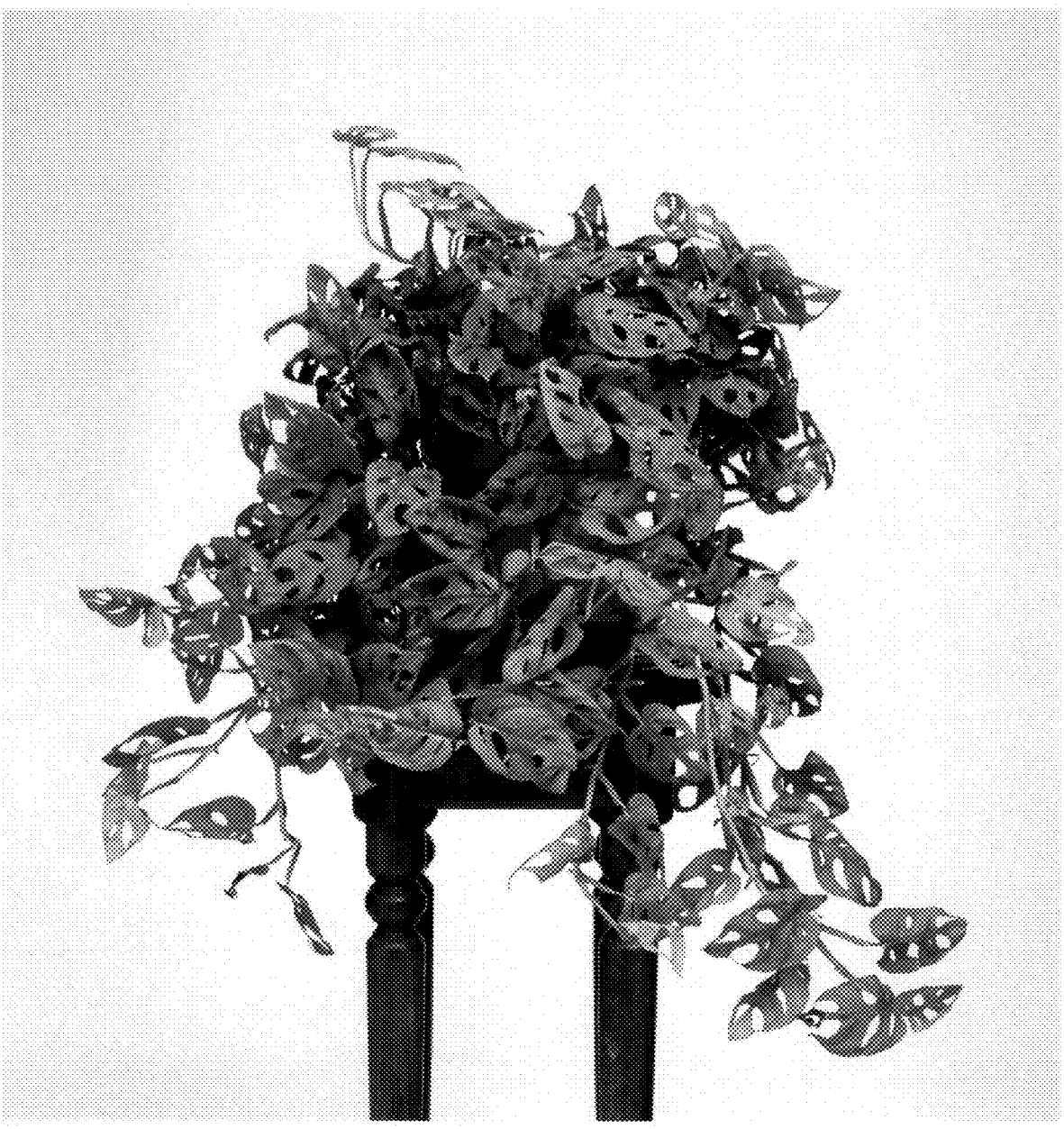

Genus and species: *Monstera adansonii* Schott.
Variety denomination: 'ELSTMN0424'.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35U.S.C. 102 (b)(1) for disclosures and/or sales that fall within a one-year grace period prior to the filing date. This application claims priority to CPVO application No. 2025/0241 filed on Feb. 4, 2025.

BACKGROUND OF THE NEW PLANT

The present invention comprises a new and distinct variety of *Monstera* plant, botanically known as *Monstera adansonii*, and hereinafter referred to by the variety name 'ELSTMN0424'. The new *Monstera* cultivar is a product of a planned breeding program located in Rijsenhout, The Netherlands. The new cultivar is a naturally occurring branch mutation originating from an unnamed and unpatented population of *Monstera adansonii* plants cultivated in a greenhouse in Rijsenhout, The Netherlands. Several mutations were selected by the inventor from said population of *Monstera adansonii* plants for over one year. The mutations were grown in 14 cm pots and observed for uniformity, stability, and distinctness as well as for their commercial potential. From amongst these mutations, 'ELSTMN0424' was selected by the inventor in September 2023 for further propagation and commercialization based on its unique plant shape, fast growth rate, compactness and small leaf size.

The new *Monstera* cultivar 'ELSTMN0424' was first reproduced asexually using meristematic tissue culture in September 2023 in Rijsenhout, The Netherlands. Asexual propagation by meristematic tissue culture of the new variety has shown that the unique features of the new variety are stable and reproduced true-to-type to date through 8 successive generations.

SUMMARY OF THE INVENTION

The new *Monstera* cultivar 'ELSTMN0424' has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Monstera* cultivar. The combination of these characteristics distinguishes 'ELSTMN0424' as a new and distinct variety of *Monstera*.

1. *Monstera* 'ELSTMN0424' exhibits leaves with numerous small-sized fenestrations creating a denser and more perforated leaf appearance.
2. *Monstera* 'ELSTMN0424' exhibits a medium green leaf coloration with no variegation.
3. *Monstera* 'ELSTMN0424' exhibits a compact and trailing growth habit with pendulous branches.

DESCRIPTION OF THE PHOTOGRAPHS

This new *Monstera* cultivar is illustrated by the accompanying-colored photographs which show the overall appearance and distinct characteristics of the plant. The colors shown are as true as can be reasonably obtained by conventional photographic procedures.

The photographs are 1-year-old plants grown in 17-centimeter circular containers in a conventional glass greenhouse in Rijsenhout, The Netherlands. Colors in the photographs may differ slightly from the color values cited in the botanical description which accurately describes the colors of the new variety.

FIG. 1. shows the overall plant form and foliage of 'ELSTMN0424'.

Figure 2:
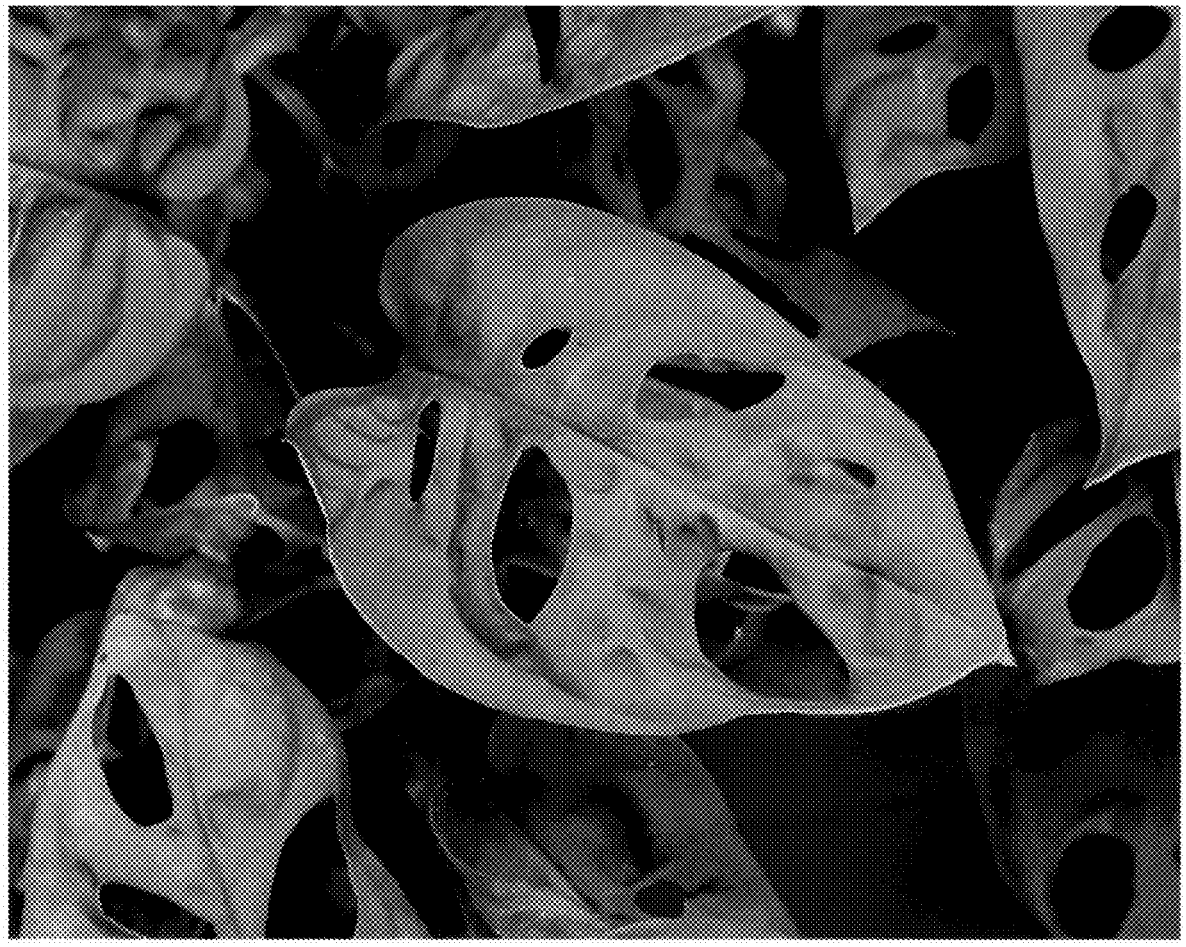

FIG. 2. shows a close-up of a typical mature leaf of 'ELSTMN0424'.

DESCRIPTION OF THE NEW VARIETY

In the following description, color references are made to The Royal Horticultural Society Colour Chart, Sixth Edition, except where general color terms of ordinary dictionary significance are used.

The following observations and measurements describe plants grown in a conventional glass greenhouse located in Rijsenhout, The Netherlands. Growing condition consisted of an average day and night temperature of 20° C. to 22° C., 60 to 85 percent relative humidity, 150-200 μmol/m$^2$/sec (PAR) of light, and 600 to 700 ppm of CO2. Detailed descriptions were taken in December 2024. from 1-year-old plants grown in 17-centimeter circular containers. Measurements and numerical values represent averages of typical plant types.

DETAILED BOTANICAL DESCRIPTION

Classification:

*Family.*—Araceae.

*Botanical.*—*Monstera adansonii.*

*Denomination.*—'ELSTMN0424'.

General Description:

*Plant type.*—Trailing tropical perennial for use as a potted ornamental plant.

*Approximate container size and/or cropping system.*—13.0 cm or larger pots.

*Growth habit.*—Trailing, pendulous.

*Overall plant shape.*—Broadly ovate with pendulous branches.

*Height from soil level to top of foliar plane.*—Average 16.6 cm, and 79.0 cm from the distal tips of the pendulous branches to the top of the foliar plain.

*Plant diameter or area of spread.*—57.5 cm.

*Growth rate.*—Moderate.

*Plant vigor.*—Moderate to high.

*Branching habit.*—Basal branching with no lateral branching.

*Aerial roots.*—Present at branch nodes, non-fibrous, tough and slightly fleshy. Length: Average 0.9 cm. Diameter: 0.2 cm. Color: 197A and 197B (greyed-green).

*Propagation type.*—Meristematic tissue culture.

Branch description:

*Number of branches or stems per plant.*—Average 20.

*Length.*—Average 35.0 cm.

*Diameter.*—0.4 cm.

*Internode length.*—2.7 cm.

*Appearance and shape.*—Rounded.

*Luster.*—Matte to very slightly glossy.

*Aspect/angle from vertical.*—90°, near horizontal at soil level with pendulous branches 0°, near vertical.

*Strength.*—Strong.

*Color.*—Developing stems: Upper surface: 144A (yellow-green). Lower surface: Lighter than upper surface, near 144C (yellow-green). Mature stems: Upper surface: NN137A (green). Lower surface: 144C (yellow-green). Internodes: Upper surface: 143C (green). Lower surface: 144C (yellow-green).

*Pubescence.*—Not present.

Foliage description:

*Arrangement.*—Alternate, simple.

*Quantity of leaves per basal clump.*—Average of 13.

*Lamina.*—Shape, description: Ovate; an average of 5 (varying between 4 and 6) holes between the secondary veins, holes shaped irregular ovate to elliptic, with an average length of 1.3 cm (varying between 0.5 cm and 2.5 cm) and with an average diameter of 0.7 cm (varying between 0.1 cm and 1.7 cm). Length: Average 8.2 cm. Width: Average 4.9 cm. Aspect: Flat to very slightly carinate. Apex shape: Apiculate. Base shape: Cordate to deep truncate, unlobed. Margins: Entire, slightly coarsely undulate. Texture: Upper surface: Smooth, glabrous. Lower surface: Smooth, glabrous, slightly velvety. Rugosity (both upper and lower surfaces): Coarsely and shallowly rugose or puckered. Pubescence: Not present. Luster: Upper surface: Very slightly glossy. Lower surface: Matte. Color: Juvenile foliage: Upper surface: 143B (green). Lower surface: A blend of 143C (green) and 144A (yellow-green). Mature foliage: Upper surface: A blend of NN137A (green) and 147A (yellow-green), with a very narrow, near transparent edge of 145D (yellow-green). Lower surface: 147B (yellow-green) with a very narrow, near transparent edge of 145D (yellow-green). Venation: Pattern: Pinnate. Color (mature leaves): Upper surface: 146A (yellow-green). Lower surface: 143C (green).

*Petiole.*—Length: Average 5.4 cm, including geniculum. Diameter: Upper side U-shaped, average 0.3 cm horizontally and vertically. Texture: Smooth, glabrous. Luster (both upper and lower surfaces): Very slightly glossy. Strength: Strong. Color: Upper surface: 137B (green). Lower surface: 143B (green). Geniculum: Length: Average 1.6 cm. Width: Average 0.2 cm. Color: 144A (yellow-green). Wings: Length: Average 4.4 cm. Width: Average 0.4 cm. Color: Inner surface: 137B and 137C (green) with a translucent narrow edge along the margin, 145D (green). Outer surface: 146A and 146B (yellow-green) with a translucent narrow edge along the margin, 145D (green).

Inflorescence: None observed to date.

High temperature tolerance: Up to 40 degrees Celsius.

Low temperature tolerance: Down to greater than 5 degrees Celsius.

USDA hardiness zones: Zones 10 to 13.

Rain tolerance: Moderate.

Wind tolerance: Low to moderate.

Disease and pest tolerance: No claims are made to any superior disease or insect resistance or tolerance.

COMPARISON WITH THE PARENT PLANT

The new *Monstera* cultivar 'ELSTMN0424' can be distinguished from its progenitor or parent plants of *Monstera adansonii* in the following characteristics described in Table 1 below.

TABLE 1

| Characteristic | 'ELSTMN0424' | *Monstera adansonii* (parent) |
|---|---|---|
| Leaf shape. | Ovate with fenestrations; slightly narrower, more elongated. | Ovate with fenestrations; broader leaf blades. |
| Leaf size. | Smaller on average, typically 8.0 to 15.0 cm in length. | Larger, typically 15.0 to 25.0 cm in length. |
| Fenestrations. | More numerous and smaller, creating a denser and more perforated appearance. | Fewer and with larger openings. |
| Leaf texture. | Slightly thicker and leatherier. | Smooth and moderately thin. |
| Growth habit. | Strong trailing/vining growth habit, cascading appearance. | Upright to semi-climbing when staked. |
| Branching. | Higher branching tendency, denser foliage. | Less branching and more spaced nodes. |
| Internode length. | Shorter, contributing to a compact, bushy appearance. | Longer, contributing to a more open plant form. |
| Overall plant appearance. | Dense and trailing with many smaller leaves and more numerous fenestrations. | Upright with fewer, but larger leaves and open fenestrations. |

COMPARISON WITH RELATED KNOWN VARIETY

The new *Monstera* cultivar 'ELSTMN0424' can be distinguished from the related known variety of *Monstera adansonii* cultivar 'Albo Variegata' (unpatented) in the following characteristics described in Table 2 below.

TABLE 2

| Characteristic | 'ELSTMN0424' | 'Albo Variegata' |
|---|---|---|
| Leaf color (upper surface). | Uniform medium green with no variegation. | Green with large sectorial and marbled white variegation, sometimes with entirely white leaves. |
| Leaf pattern. | Consistently green, fenestrations are the only patterning. | Irregular white variegation with contrasting patches and sectors of color. |
| Leaf size. | Slightly smaller on average, typically 8.0 to 15.0 cm in length. | Medium-sized, typically 10.0 to 18.0 cm in length. |
| Fenestrations. | More numerous, smaller fenestrations giving a denser perforated appearance. | Fewer but larger fenestrations, irregularly placed. |
| Leaf shape. | Ovate, slightly narrower with a more elongated appearance. | Ovate with slightly broader blades. |
| Growth habit. | Strong trailing/vining growth habit, cascading appearance. | Semi-climbing when supported, slower-growing due to leaf variegation. |
| Branching. | Higher branching tendency, denser foliage. | Less branching, more open structure. |
| Overall plant appearance. | Trailing plant with lush, uniform green foliage and with many leaf fenestrations. | Ornamental with striking green and white variegation. |

What is claimed is:

1. A new and distinct cultivar of *Monstera* plant named 'ELSTMN0424', substantially as illustrated and described herein.

* * * * *